United States Patent
Kitaoka et al.

(10) Patent No.: US 7,091,051 B2
(45) Date of Patent: Aug. 15, 2006

(54) CHEMILUMINESCENCE METHOD OF 1,2-DIOXETANE AND COMPOSITION FOR CHEMILUMINESCENCE

(75) Inventors: Kenji Kitaoka, Ebina (JP); Masashi Yamada, Yokohama (JP); Seiji Kawaguchi, Fujisawa (JP)

(73) Assignee: Tosoh Corporation, Shunan (JP)

( * ) Notice: Subject to any disclaimer, the term of this patent is extended or adjusted under 35 U.S.C. 154(b) by 0 days.

(21) Appl. No.: 10/924,980

(22) Filed: Aug. 25, 2004

(65) Prior Publication Data

US 2005/0048591 A1 Mar. 3, 2005

(30) Foreign Application Priority Data

Aug. 28, 2003 (JP) ............... 2003-304958

(51) Int. Cl.
- *G01N 33/532* (2006.01)
- *G01N 21/76* (2006.01)
- *C12Q 1/42* (2006.01)
- *C12Q 1/28* (2006.01)

(52) U.S. Cl. ............ 436/546; 436/172; 436/904; 435/968; 435/21; 435/28; 549/507; 549/497; 549/504

(58) Field of Classification Search .......... 436/546, 436/172, 904; 549/507, 497, 504; 435/968, 435/21, 28

See application file for complete search history.

(56) References Cited

U.S. PATENT DOCUMENTS

| | | | |
|---|---|---|---|
| 5,145,772 A | 9/1992 | Voyta et al. | |
| 5,731,445 A | 3/1998 | Matsumoto et al. | |
| 5,877,333 A | 3/1999 | Matsumoto et al. | |
| 5,994,073 A * | 11/1999 | Bronstein et al. | 435/6 |
| 2004/0166539 A1* | 8/2004 | Akhavan-Tafti et al. | 435/7.9 |

FOREIGN PATENT DOCUMENTS

| | | |
|---|---|---|
| JP | 5-79985 | 3/1993 |
| JP | 7-31201 | 4/1995 |
| JP | 7-91536 | 10/1995 |
| JP | 7-121237 | 12/1995 |
| JP | 8-507694 | 8/1996 |
| JP | 2648423 | 5/1997 |
| JP | 9-216887 | 8/1997 |
| JP | 11-500222 | 1/1999 |
| WO | WO 94/21821 | 9/1994 |
| WO | WO 96/25667 | 8/1996 |

* cited by examiner

*Primary Examiner*—Mary E. Ceperley
*Assistant Examiner*—Shafiqul Haq
(74) *Attorney, Agent, or Firm*—Oblon, Spivak, McClelland, Maier & Neustadt, P.C.

(57) ABSTRACT

A chemiluminescence method characterized in that when a 1,2-dioxetane derivative of the formula 1:

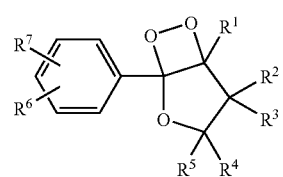

wherein each of $R^1$, $R^2$, $R^3$, $R^4$ and $R^5$ which are independent of one another, is a hydrogen atom, an alkyl group or an aryl group, or each pair of $R^2$ and $R^3$, and $R^4$ and $R^5$, which are independent of each other, may form together a cyclic alkyl group, $R^6$ is a hydroxyl group, an alkoxyl group, an aralkyloxy group, a group represented by —OSi($R^8R^9R^{10}$) (provided that each of $R^8$, $R^9$ and $R^{10}$ which are independent of one another, is an alkyl group or an aryl group), a phosphate group or a group represented by $S(C=O)R^{11}$ (provided that $R^{11}$ is an alkyl group or an aryl group), and $R^7$ is a hydrogen atom, a halogen atom, an alkyl group or an alkoxyl group, is let generate chemiluminescence by means of an activator selected from the group consisting of a base, an acid, a salt, a fluorine compound, an enzyme, a catalyst and an amine compound, a cationic surfactant and a fluorescent material are made to coexist.

25 Claims, No Drawings

CHEMILUMINESCENCE METHOD OF 1,2-DIOXETANE AND COMPOSITION FOR CHEMILUMINESCENCE

The present invention relates to a method for intensifying chemiluminescence of 1,2-dioxetane and a composition for chemiluminescence. The method according to the present invention is effective for a high-sensitive analysis for a biological component, an enzyme, a chemical product or the like, and the composition for chemiluminescence according to the present invention can suitably be used as a substrate reagent for an enzyme immunoassay.

A water-soluble chemiluminescent material having a 1,2-dioxetane structure is a very useful compound under the condition under which a protic solvent is used such as an analysis of a biological component, and the demand becomes increasingly high in recent years. However, in a case where 1,2-dioxetane is used alone in the protic solvent, only very low luminous efficiency can be obtained, and accordingly, even if it is intended to be used for immunoassay for a clinical examination, no chemiluminescence intensity which can be practically used could be obtained. Therefore, it has been necessary to intensify the chemiluminescence of water-soluble chemiluminescent dioxetane. In the present specification, materials useful to increase chemiluminescence intensity of a chemiluminescent compound are generically called as sensitizers or enhancers regardless of whether or not they are directly concerned with electronic energy transfer.

Heretofore, as the enhancers to 1,2-dioxetane which is decomposed into two carbonyl-containing compounds and discharges electronic energy to emit light, a cationic surfactant (for example JP-B-7-121237), a mixture of a cationic surfactant and a fluorescent material (JP-B-7-91536), a vinylbenzyl quaternary ammonium salt polymer (for example JP-B-7-31201) and a polycationic high-polymer phosphonium salt (Japanese Patent No. 2648423) have been proposed. Further, there is an example wherein a quaternary phosphonium salt is added to a chemiluminescence system of acridinium ester (JP-A-5-79985).

However, a 1,2-dioxetane derivative having a furan ring as represented by the formula 1 (for example JP-A-9-216887) to be used in the present invention, is a chemiluminescent material excellent in heat stability, which is not decomposed into two compounds at the time of luminescence. However, the most suitable sensitizer to increase the chemiluminescence intensity has not been reported up to now.

Under these circumstances, it is an object of the present invention to provide a chemiluminescence method, which is the most suitable for the chemiluminescence of a 1,2-dioxetane derivative having a furan ring. Further, it is an object of the present invention to provide a composition for chemiluminescence, which can also be used as a substrate reagent for an enzyme immunoassay, is excellent in heat stability, and makes a high-sensitive analysis possible.

The present inventors have conducted extensive studies on the above problems, and as a result, achieved the present invention. Namely, the present invention provides a chemiluminescence method characterized in that when a 1,2-dioxetane derivative of the formula 1:

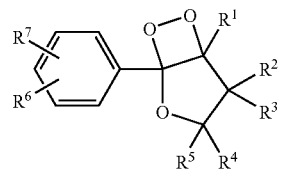

wherein each of $R^1$, $R^2$, $R^3$, $R^4$ and $R^5$ which are independent of one another, is a hydrogen atom, an alkyl group or an aryl group, or each pair of $R^2$ and $R^3$, and $R^4$ and $R^5$ which are independent of each other, may form together a cyclic alkyl group, $R^6$ is a hydroxyl group, an alkoxyl group, an aralkyloxy group, a group represented by —OSi($R^8R^9R^{10}$) (provided that each of $R^8$, $R^9$ and $R^{10}$ which are independent of one another, is an alkyl group or an aryl group), a phosphate group or a group represented by S(C=O)$R^{11}$ (provided that $R^{11}$ is an alkyl group or an aryl group), and $R^7$ is a hydrogen atom, a halogen atom, an alkyl group or an alkoxyl group, is made to generate chemiluminescence by means of an activator selected from the group consisting of a base, an acid, a salt, a fluorine compound, an enzyme, a catalyst and an amine compound, a cationic surfactant and a fluorescent material are made to coexist.

Further, the present invention provides a composition for chemiluminescence comprising a 1,2-dioxetane derivative of the above formula 1, a cationic surfactant and a fluorescent material.

Now, the present invention will be described in further detail.

Firstly, the 1,2-dioxetane derivative of the formula 1 will be described.

The alkyl group as the substituent is a $C_{1-20}$ straight chain, branched or cyclic alkyl group, and it may, for example, be a straight chain group such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl or eicosanyl, or a group having these alkyl groups appropriately bonded in a branched form or in a cyclic form. Such an alkyl group may further have a substituent. For example, it may be substituted by e.g. a hydroxyl group, an alkoxyl group or an aryl group.

As the aryl group, a $C_{6-20}$ aromatic hydrocarbon group such as a phenyl or naphthyl group, or a heteroaryl group having from 1 to 5 nitrogen atoms, oxygen atoms or sulfur atoms in the ring such as a furyl, thienyl or pyridyl group may, for example, be mentioned. As the alkoxyl group, one having from 1 to 5 $C_{1-20}$ alkoxy groups bonded in a straight chain form or in a branched form, such as methoxy, ethoxy, propoxy, butoxy, pentyloxy, hexyloxy, methoxyethoxy, methoxypropoxy, ethoxyethoxy, ethoxypropoxy or methoxyethoxyethoxy, may, for example, be mentioned. As the aralkyloxy group, a $C_{7-20}$ group such as a benzyloxy or phenethyloxy group may, for example, be mentioned. As the halogen atom, fluorine, chlorine or bromine may, for example, be mentioned.

As the 1,2-dioxetane derivative having such substituents of the formula 1, specifically, 5-t-butyl-4,4-dimethyl-l-(3'-phosphoryloxy)phenyl-2,6,7-trioxabicyclo[3.2.0]heptane disodium salt or phosphoric acid mono-[5-(5-t-butyl-4,4-dimethyl-2,6,7-trioxabicyclo[3.2.0]hept-1-yl)-2-chlorophenyl]ester disodium salt may, for example, be mentioned.

The activator to be used in the present invention is used to let the 1,2-dioxetane derivative of the formula 1 generate luminescence. It is not particularly limited so long as it is one which acts on the group $R^6$ in the 1,2-dioxetane derivative of the formula 1 to convert the derivative into a carbonyl compound via an unstable oxide intermediate and makes the derivative generate chemiluminescence at the same time. For example, if $R^6$ is a hydroxyl group, a base may suitably be used, and if $R^6$ is a group represented by —OSi($R^8R^9R^{10}$) (provided that each of $R^8$, $R^9$ and $R^{10}$ which are independent of one another, is an alkyl group or an aryl group), tetrabutylammonium fluoride may suitably be used as the activator. In a case where the 1,2-dioxetane derivative of the formula 1 is used as a substrate for an enzyme immunoassay, various enzymes such as alkaline phosphatase, arylesterase, acetylcholinesterase, peroxidase and galactosidase may suitably be used as the activator.

As the cationic surfactant to be used in the present invention, it is not particularly limited so long as it is one having an effect for intensifying chemiluminescence of the 1,2-dioxetane of the formula 1 together with a fluorescent material as mentioned hereinafter. As a suitable cationic surfactant, for example, poly(benzyltributyl)ammonium chloride contained in commercially available Emerald-II™ (manufactured by TROPIX, Inc.) or a quaternary ammonium salt or a quaternary phosphonium salt of the formula 2:

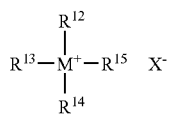

wherein one of $R^{12}$, $R^{13}$, $R^{14}$ and $R^{15}$ is a $C_{8-20}$ alkyl group or a $C_{8-20}$ aryl group, and the other three are each independently a $C_{1-8}$ alkyl group, a benzyl group or a phenyl group, $M^+$ represents a positively charged nitrogen atom or phosphorus atom, and $X^-$ represents a halogen ion may be mentioned.

In the formula 2, the $C_{8-20}$ alkyl group is a $C_{8-20}$ straight chain or branched alkyl group, and it may, for example, be a straight chain group such as octyl, nonyl, decyl, undecyl, dodecyl, tetradecyl, pentadecyl, hexadecyl, heptadecyl, octadecyl, nonadecyl or eicosanyl, or a group having these alkyl groups appropriately bonded in a branched form. The $C_{1-8}$ alkyl group is a $C_{1-8}$ straight chain or branched alkyl group, and it may, for example, be a straight chain such as methyl, ethyl, propyl, butyl, pentyl, hexyl, heptyl or octyl, or a group having these alkyl groups appropriately bonded in a branched form. As the $C_{8-20}$ aryl group, a $C_{8-20}$ aromatic hydrocarbon group such as a naphthyl group, or a heteroaryl group having from 1 to 5 nitrogen atoms, oxygen atoms or sulfur atoms in the ring may, for example, be mentioned. As the halogen ion, a fluorine ion, a chlorine ion or a bromine ion may, for example, be mentioned.

As a suitable example of the quaternary ammonium salt of the formula 2 having substituents as mentioned above, cetyl trimethylammonium bromide (CTAB), benzalkonium chloride or benzethonium chloride may be mentioned. Further, as a suitable example of the quaternary phosphonium salt, tri-n-butylhexadecylphosphonium bromide, ethyltriphenylphosphonium bromide, triheptylphenylphosphonium bromide or tetradecyltriphenylphosphonium bromide may be mentioned. Among them, tri-n-butylhexadecylphosphonium bromide is particularly preferred.

The fluorescent material to be used in the present invention is not particularly limited so long as it is one having an effect for intensifying chemiluminescence of the 1,2-dioxetane derivative of the formula 1 together with the cationic surfactant. For example, fluorescein, a fluorescein derivative (such as sodium fluorescein, aminofluorescein or fluorescein isothiocyanate (FITC)), a Bodipy dye, Oregon Green 488, Oregon Green 514, Rhodol Green (trademark), Alexa Fluor 488 (trademark), hydrazide or 5-(or 6-)-carboxy-2', 7'-dichlorofluorescein may be mentioned. Among them, fluorescein is particularly preferred.

In the present invention, the concentration of the 1,2-dioxetane derivative to be used may appropriately be determined within a range where the measured value relative to standard solutions having a zero concentration and a positive concentration of the object to be measured satisfies a measured value-to-concentration approximately linear relation. The concentration can suitably be set to a range of from 0.1 to 1.2 mM. In the concentration region having a remarkably lower concentration than the above range, the measured value relative to the positive concentration tends to be on a plateau, and the upper limit of the measurement range tends to be low. On the contrary, in the concentration region having a remarkably higher concentration than the above range, a background in the measured value relative to the zero concentration will increase, and the detection sensitivity in the low concentration region of the object to be measured tends to deteriorate.

The concentration of the cationic surfactant to be used is suitably within a range of from 0.0025% to 2.0%. In order to obtain the most suitable luminescence amount, it is particularly preferably from 0.01 to 0.10%. As for the concentration of the fluorescent material to be used, if the concentration of the 1,2-dioxetane derivative is high, it will be required to be proportionately high. However, it is preferably from about 0.0025 to about 0.25% in order to increase the sensitizing effect.

In the present invention, the cationic surfactant and the fluorescent material are made to coexist when the 1,2-dioxetane derivative of the formula 1 is made to generate chemiluminescence by means of the above activator. Accordingly, the same or larger luminescence amount than that of a conventional method can be obtained.

The detection of the chemiluminescence is not particularly limited. For example, all the above respective components, namely, the 1,2-dioxetane derivative, the cationic surfactant, the fluorescent material and the activator are brought into contact, followed by incubation, and the reaction solution is introduced into a luminescence detector after a certain period of time. As the luminescence detector, a luminometer provided with single photon counter is suitably used. When luminescence having high intensity is obtained by means of a sensitizer or the like, a silicon photodiode or a photographic film can be used. When an enzyme is used as the activator, an enzyme reaction stopper may be added before the reaction solution is introduced into the luminescence detector.

Further, the chemiluminescence reaction which proceeds simultaneously with the progress of the enzyme reaction may be continuously monitored to measure the increasing rate of the luminescence amount. If the increasing rate is within a range of a certain period of time, it will not be required to strictly define the time between the beginning of the enzyme reaction i.e. the beginning of the chemiluminescence reaction and the luminescence detection. In a case where the chemiluminescence reaction is continuously monitored, the optimum pH of the enzyme reaction with a chemiluminescent substrate and the optimum pH of the chemiluminescence reaction which occurs successively preferably agree with each other as far as possible. For example, when the activator is an alkaline phosphatase, the optimum pH of the enzyme reaction substantially agree with the optimum pH of the chemiluminescence reaction, and a 2-amino-2-methyl-1-propanol buffer solution or a diethanolamine buffer solution having a pH of about 10 may suitably be used.

On the other hand, the composition for chemiluminescence of the present invention is one comprising the 1,2-dioxetane derivative of the formula 1, the cationic surfactant and the fluorescent material. Further, it may appropriately contains a pH adjustor or a preservative such as sodium azide to secure the storage stability. The composition for chemiluminescence may be used as a solid, or it may be used in the form of a solution, for example, by dissolving it in an aqueous buffer solution.

The luminescence method according to the present invention makes it possible to obtain the same or larger luminescence amount than that of a conventional method. Particularly when tri-n-butylhexadecylphosphonium bromide is used as the cationic surfactant, a luminescence amount larger than that of a conventional method can be obtained. Further, the composition for chemiluminescence according to the present invention, when the activator is made to act thereon, not only makes it possible to obtain the same or larger luminescence amount than that of a conventional method but also maintains extremely high storage stability.

EXAMPLES

Now, the present invention will be described in further detail with reference to Examples. However, it should be understood that the present invention is by no means limited to such specific Examples.

Examples 1 to 11

A 5-membered dioxetane phosphate (formal name: 5-t-butyl-4,4-dimethyl-1-(3'-phosphoryloxy)phenyl-2,6,7-trioxabicyclo[3.2.0]heptane disodium salt) of the formula 3:

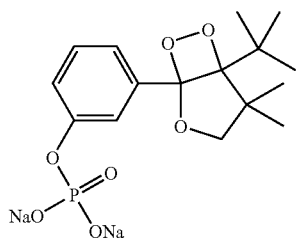

3 was produced in accordance with JP-A-9-216887 and purified by using a chelate resin. To a 0.1 to 0.2 M 2-amino-2-methyl-1-propanol buffer solution (pH 10.0) or diethanolamine buffer solution (pH 10.0) comprising 0.4 mM of the dioxetane phosphate thus obtained, fluorescein at a concentration as shown in Table 1 as a fluorescent material and 0.02% sodium azide, a cationic surfactant as shown in Table 1 was added to have a concentration as shown in Table 1. The solution is considered as a composition solution for chemiluminescence. Further, in Example 11, a commercially available Emerald-II™ (manufactured by TROPIX, INC.; containing poly(benzyltributyl)ammonium chloride as a cationic surfactant and sodium fluorescein as a fluorescent material) was used as the fluorescent material and the cationic surfactant.

50 μL of the composition solution for chemiluminescence was reacted with 10 μL of a 50 mM Tris-HCl buffer solution containing $10^{-18}$ mol/mL of alkaline phosphatase, a 0.1% gelatin hydrolyzate, 1 mM $MgCl_2$, 0.15 M NaCl and 0.05% sodium azide, and the luminescence amount was measured. Luminometer LB96V (detector: single photon counter; measured wavelength-region: from 380 to 630 nm) manufactured by BERTHOLD TECHNOLOGIES GmbH and Co, KG was used for the luminescence measurement, and as the luminescence measuring condition, the luminescence amount (count) was measured for 1 second 5 minutes after the composition for chemiluminescence and the above enzyme solution were mixed. The results are shown in Table 1. Further, the ratio of the luminescence amount based on the luminescence amount in Comparative Example 1 as mentioned hereinafter (in which the surfactant and the fluorescent material were not added) is shown as the amplification rate in the rightmost column in Table 1.

As evident from Table 1, the amplification rate of luminescence was at least 10 times in any case where the cationic surfactant was added. Further, when hexadecyltrimethylammonium bromide (CTAB) and tetradecyltrimethylammonium chloride which are quaternary ammonium salts having three methyl groups were compared with tetradecyldimethylbenzylammonium chloride (benzalkonium chloride) and hexadecyldimethylbenzylammonium chloride having one of the above methyl groups replaced by a benzyl group, the latter showed higher amplification rates. That is, if the hydrophobicity of the substituents in the hydrophilic moiety in the vicinity of $N^+$ is increased, the amplification rate of luminescence tended to increase.

Further, when triphenylphosphonium salts (ethyl, n-heptyl and n-tetradecyl) were compared with one another, such a result was shown that the longer the alkyl chain is, the higher the amplification rate of luminescence becomes. When tri-n-butylhexadecylphosphonium bromide having a tri-n-butyl group having high hydrophobicity as the substituent in the hydrophilic moiety and having a hexadecyl group as a long chain alkyl group was used, the highest amplification rate of 430.49 times was recorded. This value was higher than the amplification rate of 97.53 times in a case where Emerald-II™ which is commercially available as the enhancer was used.

Comparative Examples 1 to 8

The same operation as in Example 1 was carried out except that the surfactant and the fluorescent material were not added in Comparative Example 1, and an anionic, nonionic or amphoteric surfactant as shown in Table 1 having a concentration as shown in Table 1 was used instead of the cationic surfactant in Comparative Examples 2 to 8. The results are shown in Table 1.

In the case where SDS (sodium dodecyl sulfate) as the anionic surfactant (Comparative Example 2); Triton X-100 (Comparative Example 3), Tween 80 (Comparative Example 4) or Tween 20 (Comparatives Example 5) as the nonionic surfactant; or n-dodecyldimethyl (3-sulfopropyl) ammonium hydroxide (Comparative Example 6), CHAPS (3-[(3-cholamidopropyl)dimethylammonio]-1-propane sulfonate) (Comparative Example 7) or CHAPSO (3-[(3-cholamidopropyl)dimethylammonio]-2-hydroxy-1-propane sulfonate) (Comparative Example 8) as the amphoteric surfactant was used, the luminescence amplification rate was at most 5 times as compared with Comparative Example 1, in which the surfactant and the fluorescent material were not added, and substantially no effect was obtained.

Comparative Examples 9 and 10

For comparison with commercial products, the luminescence amount was measured in each of cases where a chemiluminescence substrate CSPD (trademark) (manufactured by TROPIX, INC., a 1,2-dioxetane compound having no furan ring) was used instead of the composition solution for chemiluminescence of Example 1, and the surfactant and the fluorescent material were not used (Comparative Example 9), and CSPD (trademark) (manufactured by TROPIX, INC., a 1,2-dioxetane compound having no furan ring) having Emerald II™ (manufactured by TROPIX, INC., containing poly(benzyltributyl)ammonium chloride as the cationic surfactant and sodium fluorescein as the fluorescent material) added thereto was used instead of the composition solution for chemiluminescence of Example 1 (Comparative Example 10). The results are shown in Table 2. The ratios of the luminescence amount of the former and the latter were shown in the rightmost column in Table 2 as the amplification rate.

TABLE 1

|  | Surfactant | Surfactant addition amount (wt %) | Fluorescent material addition amount (wt %) | Luminescence amount (count) | Amplification rate (times) |
| --- | --- | --- | --- | --- | --- |
| Example 1 | Benzethonium chloride | 0.05 | 0.005 | 34,324 | 59.38 |
| Example 2 | Hexadecyltrimethylammonium bromide (CTAB) | 0.031 | 0.0025 | 90,913 | 157.29 |
| Example 3 | Tetradecyltrimethylammonium chloride | 0.063 | 0.0025 | 91,496 | 158.30 |
| Example 4 | Tetradecyldimethylbenzylammonium chloride (benzalkonium chloride) | 0.025 | 0.0025 | 102,067 | 176.59 |
| Example 5 | Hexadecyldimethylbenzylammonium chloride (Cetol) | 0.025 | 0.0025 | 115,312 | 199.50 |
| Example 6 | Tetra-n-butylphosphonium bromide | 0.25 | 0.025 | 7,191 | 12.44 |
| Example 7 | Ethyltriphenylphosphonium bromide | 1.25 | 0.025 | 6,960 | 12.04 |
| Example 8 | n-Heptyltriphenylphosphonium bromide | 1.25 | 0.025 | 12,395 | 21.44 |
| Example 9 | n-Tetradecyltriphenylphosphonium bromide | 0.025 | 0.0025 | 50,662 | 87.65 |
| Example 10 | Tri-n-butylhexadecylphosphonium bromide | 0.025 | 0.0025 | 248,825 | 430.49 |
| Example 11 | Poly(benzyltributyl)ammonium chloride | <0.2* | <0.2* | 56,374 | 97.53 |
| Comparative Example 1 | Not added | — | — | 578 | — |
| Comparative Example 2 | SDS (sodium dodecyl sulfate) | 0.0025 | 0.025 | 1,463 | 2.53 |
| Comparative Example 3 | Triton X-100 | 0.0025 | 0.025 | 1,361 | 2.35 |
| Comparative Example 4 | Tween 80 | 0.0025 | 0.025 | 1,100 | 1.90 |
| Comparative Example 5 | Tween 20 | 0.0025 | 0.025 | 1,125 | 1.95 |
| Comparative Example 6 | n-Dodecyldimethyl(3-sulfopropyl)ammonium hydroxide | 0.025 | 0.0025 | 988 | 1.71 |
| Comparative Example 7 | CHAPS | 0.92 | 0.0025 | 2,214 | 3.83 |
| Comparative Example 8 | CHAPSO | 0.95 | 0.0025 | 2,464 | 4.26 |

*Calculated from catalog value

TABLE 2

|  | Types of substrate/surfactant/ fluorescent material | Surfactant addition amount (wt %) | Fluorescent material addition amount (wt %) | Luminescence amount (count) | Amplification rate (times) |
| --- | --- | --- | --- | --- | --- |
| Comparative Example 9 | CSPD (commercial product)/ Nil/Nil | — | — | 541 | — |
| Comparative Example 10 | CSPD (commercial product)/ poly(benzyltributyl)ammonium chloride/sodium fluorescein | <0.2* | <0.2* | 164,088 | 303.30 |

*Calculated from catalog value

Examples 12 and 13

The composition solution for chemiluminescence prepared in Example 10 (Example 12) and the composition solution for chemiluminescence prepared in Example 4 (Example 13) were stored for 4 days under the light shielding condition in an incubator at 4° C. and 40° C., respectively, for storage stability test. Then, 50 μL of each of the solutions was reacted with 10 μL of an enzyme solution containing $10^{-18}$ mol/mL of alkaline phosphatase, 50 mM of Tris-HCl, a 0.1% gelatin hydrolyzate, 1 mM $MgCl_2$, 0.15 M NaCl and 0.05% $NaN_3$, and the luminescence amount was measured. Luminometer LB96V manufactured by BERTHOLD TECHNOLOGIES GmbH and Co. KG was used for the luminescence measurement, and the luminescence amount (count) was measured for 1 second 5 minutes after the beginning of the above reaction as the luminescent measuring condition. The results are shown in Table 3. As evident from Table 3, the luminescence amounts were 97.5% (Example 12) and 101.5% (Example 13), respectively, even after storage for 4 days at 40° C., and substantially no decrease of the luminescence amount was observed.

Comparavetive Example 11

The same operation as in Example 12 was carried out except that CSPD (trademark) (manufactured by TROPIX) having Emerald-II™ added thereto, used in Comparative Example 10 was used instead of the composition solution for chemiluminescence. The results are shown in Table 3. As evident from Table 3, after storage for 4 days at 40° C., the luminescence amount deceased to 86.6% of that after storage for 4 days at 4° C.

TABLE 3

|  |  | Example 12 | Example 13 | Comparative Example 11 |
|---|---|---|---|---|
| Type of substrate |  | Substrate according to the present invention* | Substrate according to the present invention* | CSPD |
| Surfactant |  | Tri-n-butylhexadecyl phosphonium bromide | Tetradecyldimethyl-benzylammonium chloride (benzalkonium chloride) | Poly(benzyl-tributyl) ammonium chloride |
| Luminescence amount (count) | 4° C. (1) | 204,393 | 78,011 | 140,896 |
|  | 40° C. (2) | 199,368 | 79,189 | 121,995 |
| (2)/(1) |  | 97.5% | 101.5% | 86.6% |

*5-t-Butyl-4,4-dimethyl-1-(3'-phosphoryloxy)phenyl-2,6,7-trioxabicyclo[3.2.0]heptane disodium salt The entire disclosure of Japanese Patent Application No. 2003-304958 filed on Aug. 28, 2003 including specification, claims and summary are incorporated herein by reference in its entirety.

What is claimed is:

1. A chemiluminescence method comprising activating a 1,2-dioxetane derivative of the formula 1 by contacting said 1,2-dioxetane derivative with an activator, wherein said 1,2-dioxetane derivative has a structure of:

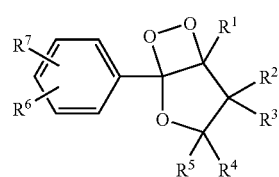

wherein each of $R^1$, $R^2$, $R^3$, $R^4$ and $R^5$ which are independent of one another, is a hydrogen atom, an alkyl group or an aryl group, or each pair of $R^2$ and $R^3$, and $R^4$ and $R^5$, which are independent of each other, may form together a cyclic alkyl group, $R^6$ is a hydroxyl group, an alkoxyl group, an aralkyloxy group, a group represented by $-OSi(R^8R^9R^{10})$ (provided that each of $R^8$, $R^9$ and $R^{10}$ which are independent of one another, is an alkyl group or an aryl group), a phosphate group or a group represented by $S(C=O)R^{11}$ (provided that $R^{11}$ is an alkyl group or an aryl group), and $R^7$ is a hydrogen atom, a halogen atom, an alkyl group or an alkoxyl group, is wherein said activator converts the R6 group on said 1,2-dioxetane derivative into a carbonyl compound via an unstable oxide intermediate, said activator being selected from the group consisting of a base, an acid, a salt, a fluorine compound, an enzyme and a catalyst, and wherein said 1,2-dioxetane derivative is in a composition comprising, in addition to said 1,2-dioxetane derivative, a cationic surfactant and a fluorescent material.

2. The method according to claim 1, wherein the cationic surfactant is a quaternary ammonium salt or a quaternary phosphonium salt of the formula 2:

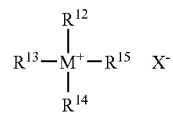

wherein one of $R^{12}$, $R^{13}$, $R^{14}$ and $R^{15}$ is a $C_{8-20}$ alkyl group or a $C_{8-20}$ aryl group, and the other three are each independently a $C_{1-8}$ alkyl group, a benzyl group or a phenyl group, $M^+$ represents a positively charged nitrogen atom or phosphorus atom, and $X^-$ represents a halogen ion.

3. The method according to claim 1, wherein the cationic surfactant is tri-n-butylhexadecylphosphonium bromide.

4. A composition for chemiluminescence comprising a 1,2-dioxetane derivative of the formula 1, a cationic surfactant and a fluorescent material,
wherein said 1,2-dioxetane derivative has a structure of:

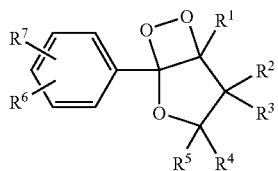

1

(wherein each of $R^1$, $R^2$, $R^3$, $R^4$ and $R^5$ which are independent of one another, a hydrogen atom, an alkyl group or an aryl group, or each pair of $R^2$ and $R^3$, and $R^4$ and $R^5$, which are independent of each other, may form together a cyclic alkyl group, $R^6$ is a hydroxyl group, an alkoxyl group, an aralkyloxy group, a group represented by $-OSi(R^8R^9R^{10})$ (provided that each of $R^8$, $R^9$ and $R^{10}$ which are independent of one another, is an alkyl group or an aryl group), a phosphate group or a group represented by $S(C=O)R^{11}$ (provided that $R^{11}$ is an alkyl group or an aryl group), and $R^7$ is a hydrogen atom, a halogen atom, an alkyl group or an alkoxyl group).

5. The composition for chemiluminescence according to claim 4, wherein the cationic surfactant is a quaternary ammonium salt or a quaternary phosphonium salt of the formula 2:

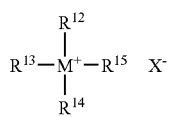

2 wherein one of $R^{12}$, $R^{13}$, $R^{14}$ and $R^{15}$ is a $C_{8-20}$ alkyl group or a $C_{8-20}$ aryl group, and the other three are each independently a $C_{1-8}$ alkyl group, a benzyl group or a phenyl group, $M^+$ represents a positively charged nitrogen atom or phosphorus atom, and $X^-$ represents a halogen ion.

6. The composition for chemiluminescence according to claim 4, wherein the cationic surfactant is tri-n-butylhexadecylphosphonium bromide.

7. The method according to claim 1, wherein said 1,2-dioxetane derivative is selected from the group consisting of 5-t-butyl-4,4-dimethyl-1-(3'-phosphoryloxy)phenyl-2,6,7-trioxabicyclo[3.2.0]heptane disodium salt and phosphoric acid mono-[5-(5-t-butyl-4,4-dimethyl-2,6,7-trioxabicyclo[3.2.0]hept-1-yl)-2-chlorophenyl]ester disodium salt.

8. The method according to claim 1, wherein said activator is an enzyme and said enzyme is selected from the group consisting of an alkaline phosphatase, an arylesterase, an acetylcholinesterase, a peroxidase, and a galactosidase.

9. The method according to claim 1, wherein said fluorescent material is selected from the group consisting of fluorescein, a fluorescein derivative, a BODIPY DYE, OREGON GREEN 488, OREGON GREEN 514, RHODOL GREEN, ALEXA FLUOR 488, hydrazide, and 5-(or 6-)-carboxy-2',7'-dichlorofluorescein.

10. The method according to claim 1, wherein the concentration of said 1,2-dioxetane derivative in said composition ranges from 0.1 mM to 1.2 mM.

11. The method according to claim 1, wherein the concentration of said cationic surfactant in said composition ranges from 0.0025% to 2.0%.

12. The method according to claim 1, wherein the concentration of said fluorescent material in said composition ranges from 0.0025% to 0.25%.

13. The method according to claim 2, wherein said cationic surfactant is a quaternary ammonium salt of formula 2.

14. The method according to claim 13, wherein said quaternary ammonium salt of formula 2 is selected from the group consisting of cetyl trimethylammonium bromide (CTAB), benzalkonium chloride, and benzethonium chloride.

15. The method according to claim 2, wherein said cationic surfactant is a quaternary phosphonium salt of formula 2.

16. The method according to claim 15, wherein said quaternary phosphonium salt of formula 2 is selected from the group consisting of tri-n-butylhexadecylphosphonium bromide, ethyltriphenylphosphonium bromide, triheptylphenylphosphonium bromide, and tetradecyltriphenylphosphonium bromide.

17. The composition according to claim 4, wherein said 1,2-dioxetane derivative is selected from the group consisting of 5-t-butyl-4,4-dimethyl-1-(3'-phosphoryloxy)phenyl-2,6,7-trioxabicyclo[3.2.0]heptane disodium salt and phosphoric acid mono-[5-(5-t-butyl-4,4-dimethyl-2,6,7-trioxabicyclo[3.2.0]hept-1-yl)-2-chlorophenyl]ester disodium salt.

18. The composition according to claim 4, wherein said fluorescent material is selected from the group consisting of fluorescein, a fluorescein derivative, a BODIPY DYE, OREGON GREEN 488, OREGON GREEN 514, RHODOL GREEN, ALEXA FLUOR 488, hydrazide, and 5-(or 6-)-carboxy-2',7'-dichlorofluorescein.

19. The composition according to claim 4, wherein the concentration of said 1,2-dioxetane derivative in said composition ranges from 0.1 mM to 1.2 mM.

20. The composition according to claim 4, wherein the concentration of said cationic surfactant in said composition ranges from 0.0025% to 2.0%.

21. The composition according to claim 4, wherein the concentration of said fluorescent material in said composition ranges from 0.0025% to 0.25%.

22. The composition according to claim 5, wherein said cationic surfactant is a quaternary ammonium salt of formula 2.

23. The composition according to claim 22, wherein said quaternary ammonium salt of formula 2 is selected from the group consisting of cetyl trimethylammonium bromide (CTAB), benzalkonium chloride, and benzethonium chloride.

24. The composition according to claim 4, wherein said cationic surfactant is a quaternary phosphonium salt of formula 2.

25. The composition according to claim 24, wherein said quaternary phosphonium salt of formula 2 is selected from the group consisting of tri-n-butylhexadecylphosphonium bromide, ethyltriphenylphosphonium bromide, triheptylphenylphosphonium bromide, and tetradecyltriphenylphosphonium bromide.

* * * * *